United States Patent
Dan et al.

(10) Patent No.: US 8,180,426 B2
(45) Date of Patent: May 15, 2012

(54) METHOD FOR TRANSFORMING HEAD SURFACE COORDINATES TO BRAIN SURFACE COORDINATES AND TRANSCRANIAL BRAIN FUNCTION MEASURING METHOD USING THE TRANSFORMATION DATA

(75) Inventors: Ippeita Dan, Tsukuba (JP); Kuniko Sakamoto, Tsukuba (JP); Masako Okamoto, Tsukuba (JP); Seiichiro Isobe, Tsukuba (JP); Kaoru Kohyama, Tsukuba (JP); Koji Shimizu, Kyoto (JP); Kazuhiro Takeo, Kyoto (JP)

(73) Assignees: Shimadzu Corporation, Nakagyo-Ku (JP); National Food Research Institute, Tsukuba-Shi Ibaraki (JP)

( * ) Notice: Subject to any disclaimer, the term of this patent is extended or adjusted under 35 U.S.C. 154(b) by 596 days.

(21) Appl. No.: 10/579,463

(22) PCT Filed: Nov. 12, 2004

(86) PCT No.: PCT/JP2004/016820
§ 371 (c)(1),
(2), (4) Date: Feb. 8, 2007

(87) PCT Pub. No.: WO2005/046484
PCT Pub. Date: May 26, 2005

(65) Prior Publication Data
US 2007/0282189 A1    Dec. 6, 2007

(30) Foreign Application Priority Data
Nov. 13, 2003   (JP) .................... 2003-384369

(51) Int. Cl.
*A61B 5/05*   (2006.01)

(52) U.S. Cl. ......... 600/407; 600/409; 600/410; 382/128
(58) Field of Classification Search ............. 600/476, 600/478, 479
See application file for complete search history.

(56) References Cited

U.S. PATENT DOCUMENTS

| | | | |
|---|---|---|---|
| 5,038,285 A * | 8/1991 | Jouandet | 382/131 |
| 5,291,888 A * | 3/1994 | Tucker | 600/383 |
| 6,611,698 B1 * | 8/2003 | Yamashita et al. | 600/310 |
| 2003/0050527 A1 * | 3/2003 | Fox et al. | 600/13 |

FOREIGN PATENT DOCUMENTS
JP   3-60638   3/1991
(Continued)

OTHER PUBLICATIONS

Towle et al "the spatial location electrodes: locating the best fitting sphere relative to cortical anatomy", Aug. 24, 1992.*

(Continued)

*Primary Examiner* — Tse Chen
*Assistant Examiner* — Joel F Brutus
(74) *Attorney, Agent, or Firm* — Edwards Wildman Palmer LLP; David J. Silvia (57) ABSTRACT

Data collected by a transcranial brain function measuring/stimulating method is accurately projected and displayed onto a brain surface. If there is no three-dimensional head image, data is projected and displayed onto the brain surface of a standard brain. The head surface coordinates are transformed to the brain surface coordinates of the brain surface underlying the head surface by, e.g., a minimum distance search method. The coordinates of a projected point on the brain surface of the head surface and the probability distribution are determined for a standard brain normalized with data on subjects.

14 Claims, 8 Drawing Sheets

FOREIGN PATENT DOCUMENTS

| | | |
|---|---|---|
| JP | 3-113685 | 5/1991 |
| JP | 03-272738 | 12/1991 |
| JP | 4-35642 | 2/1992 |
| JP | 09-019408 | 1/1997 |
| JP | 09-098972 | 4/1997 |
| JP | 2001-198112 | 7/2001 |

OTHER PUBLICATIONS

Lagerlund et al "determination of 10-20 system electrode locations using magnetic resonance image scanning with markers", Aug. 24, 1992.*

Japanese Office Action dated Feb. 17, 2009 issued in JP 2003-384369.

Towle et al; "The spatial location of EEG electrodes: locating the best-fitting sphere relative to cortical anatomy;" *Electroencephalography and clinical Neurophysiology*; vol. 86, pp. 1-6. (1993) (discussed in the specification).

Lagerlund et al; "Determination of 10-20 system electrode locations using magnetic resonance image scanning with markers;" *Electroencephalography and clinical Neurophysiology*; vol. 86, pp. 7-14. (1993) (discussed in the specification).

* cited by examiner

METHOD FOR TRANSFORMING HEAD SURFACE COORDINATES TO BRAIN SURFACE COORDINATES AND TRANSCRANIAL BRAIN FUNCTION MEASURING METHOD USING THE TRANSFORMATION DATA

BACKGROUND OF THE INVENTION

1. Field of the Invention

The present invention relates to a method for estimating brain surface coordinates relating to measurement/stimulation in near-infrared spectroscopy (NIRS), a transcranial magnetic stimulator (TMS), and the other transcranial brain function measuring/stimulating methods; its software program; and a transcranial brain function measuring apparatus for displaying measuring/stimulating results using the brain surface coordinates estimated by the methods; and more particularly to a method for projecting measurement data developed on a head surface as arbitrary points on the head surface or its set onto a brain surface underlying the head surface to express them; the software program therefor; and an apparatus therefor.

2. Description of the Related Art

In order to find positions on brain surface being objects of measurement/stimulation in a transcranial brain function measuring/stimulating method, it is required to obtain a structural image of the brain in each case by using a brain imaging procedure such as an application of a nuclear magnetic resonance apparatus (MRI). However, such a brain imaging procedure is complicated, and specific equipment is required. Thus, a method for finding positional correspondences more easily between a head surface and its brain surface is desired.

Heretofore, such a study that positions at which electrodes are disposed on a head surface are intended to correlate to a brain surface structure underlying the head surface has been made in a field of brain wave study. The most typical method in the fields of research is a sphere fitting method (see Non-Patent Literatures 1 and 2). The sphere fitting method is the one wherein a brain surface and its head surface are applied to spheres each having the same center as that of the other. According to the sphere fitting method, when a radius of the sphere representing the head surface is designated by r1, while when a radius of the sphere representing the brain surface is designated by r2, an arbitrary point on the head surface may be expressed as a polar coordinate point (r1, $\phi$, $\theta$); and a brain surface point corresponding to the head surface point can be obtained by replacing r1 by r2.

The sphere fitting method is suitable for brain wave study. However, since non-spherical head surface and brain surface are applied to spheres in the sphere fitting method, there is a problem of an appearance of a spatial distortion. In brain wave studies, since a presumption of signal sources of brain waves is conducted with a low spatial resolution in a three-dimensional space, there is not a particular problem from a practical point of view, even if there is any deviance in correspondences between the brain surface and the head surface. In other transcranial brain function measuring/stimulating methods, however, a projective method having a higher spatial resolution is desired.

In even a case where a brain image exists as a result of an imaging procedure by means of MRI and the like, a basic manner for allowing arbitrary points on a head surface to be in response to points on the brain surface underlying the head surface has not yet been established, so that a development for a correct projection method is desired.

Non-Patent Literature 1: Towle, V. L, Bolanos, J., Suarez, D., Tan, K., Grzeszczuk, R, Levin, D. N., Cakmur, R, Frank, S. A. and Spire, J. P. 1993. The spatial location of EEG electrodes: locating the best-fitting sphere relative to cortical anatomy. Electroencephalogr. Neurophysiol. 86: 1-6.

Non-Patent Literature 2: Lagerlund, T. D., Sharbrough, F. W., Jack, C. R. Jr., Erickson, B. J., Strelow, D. C., Cicora, K. M. and Busacker, N. E. 1993. Determination of 10-20 system electrode locations using magnetic resonance image scanning with markers. Electroencephalogr. Clin. Neurophysiol. 86: 7-14.

SUMMARY OF THE INVENTION

Problems to be Solved by the Invention

The present invention has been made in view of the actual state of such technology. A first object of the invention is to correctly project data obtained by a transcranial brain function measuring/stimulating method on a brain surface by determining responsive projection points on the brain surface corresponding to arbitrary points on a head surface in a head three-dimensional image containing the head surface and the brain surface.

A second object of the present invention is to make positions on a head surface to be convertible on arbitrarily three-dimensional brain coordinates as a probability distribution through standard points on the head surface in even a condition wherein no head three-dimensional image of a subject is obtained.

A third object of the present invention is to make measurement data to be able to correctly display on a brain surface in a transcranial brain function measuring apparatus.

Means for Solving the Problems

The present invention for achieving the first object is a method and a software program therefor for transforming head surface coordinates to brain surface coordinates, characterized by projecting arbitrary positions on a head surface in a three-dimensional head image onto positions on brain surface underlying the positions on head surface, and determining three-dimensional coordinate positions of the projected points.

Since there is an individual difference in structures of a brain and its head surface, it is desired that data integration is possible among a plurality of subjects in order to integrate data obtained by a transcranial brain function measuring/stimulating method among different subjects in a case even where points on the head surface have been allowed to correspond to points on the brain surface in accordance with the method of the present invention.

For this reason, it is preferred that brain surface coordinates determined with respect to a plurality of subjects are normalized to a standard brain in order to express positions on the brain surface in a standardized format.

Although it is preferred to apply MINI (Montreal Neurological Institute) coordinates or Talairach coordinates used generally in this field as such a standard brain as described above, the other coordinate systems may also be applied.

In studying methods for projecting arbitrary positions on head surface onto positions on brain surface underlying the head surface from a viewpoint of various angles, such novel finding that it is possible to make correctly the arbitrary positions on a head surface corresponding to positions on the brain surface underlying the head surface in accordance with a minimum distance search method, a perpendicular projection method, or a head surface/reference dotted line segment connecting method, and such procedure can be executed by a corresponding software program has been obtained. In this connection, the optimum method may be applied in response to a use application required among these methods.

Further during studying methods for projecting arbitrary positions on head surface onto the positions on brain surface underlying the head surface from a viewpoint of various angles, such novel finding that it is possible to express the arbitrary positions on a head surface as a relative positional relationship with respect to standard points on the head surface, and such procedure can be executed by a corresponding software program has been obtained. In this connection, the method may be used alone and it can be expressed also on arbitrary points on the head surface, or it is also possible to express as positions projected on the brain surface by combining the method with a minimum distance search method, a perpendicular projection method, or a head surface/brain interior reference dotted line segment connecting method.

A preferred aspect of the present invention relates to a software program based on a method wherein images of a plurality of markers set up at positions on the head surface and brain surface images are simultaneously taken in order to project the positions on the head surface onto the positions on the brain surface underlying the head surface, and the positions on the brain surface underlying the positions on the head surface at which the respective markers are positioned are determined by the minimum distance search method.

In the minimum search method, equidistant spheres each having a different radius from an arbitrary point on a head surface in a three-dimensional head image are drawn, and contact points of the spheres and the brain surface are determined. In the case where the head surface is positioned in the vicinity of a protrusion of the brain surface, one point having the minimum distance can be determined, while two or more points are determined in the case where the head surface is positioned in the vicinity of a depression of the brain surface. In the latter case, the center of gravity of these points is supposed to be the virtual minimum point, a straight line passing through the virtual minimum point from the head surface point in question is drawn, and an intersection point of the straight line and the brain surface is decided to be a point underlying the head surface point in question. All of these procedures can be executed as a software program. The minimum distance search method is particularly effective for processing head region image data which has not yet been processed.

The minimum distance search method is not limited to such unprocessed head region image data processing, but it is also effective for the head surface and brain surface image processing which has been subjected to smoothing processing. The smoothing processing can be carried out by a brain image processing program such as MRIcro, or the other three-dimensional image processing programs which have been commonly used widely.

The present invention includes a convex polyhedron/convex hull fitting of the head surface and brain image, and a polyhedron/hull fitting method for activating the minimum distance search method. In the case where the head surface and brain images are fit to the convex polyhedron/convex hull, one point having the minimum distance to the convex polyhedron/convex hull fitted to the brain surface is determined with respect to an arbitrary point of the convex polyhedron/convex hull fitted to the head surface. When the minimum distance obtained in the above description is expressed as a straight line, and the straight line is superposed on original head surface and brain surface images prior to the fitting to determine an intersection point with the straight line, more accurate coordinates of the brain surface and head surface points can be determined.

When such a manner that one point is generally determined from an arbitrary point of polyhedron/hull, and the point residing inside thereof takes the minimum distance with respect to the convex polyhedron/convex hull is used, the head surface can be fitted also to more complicated polyhedron/hull than the convex polyhedron/convex hull. In this case also, it is possible to determine one point on the brain surface corresponding to an arbitrary point on the head surface by means of the minimum distance search method.

Since a brain surface structure is more complicated than a head surface structure, it is also effective that the brain surface is fitted to polyhedron/hull and the head surface is fitted to convex polyhedron/convex hull. In this case, when such topological transformation that the polyhedron/hull fitted to the brain surface are expanded and the convex polyhedron/convex hull fitted to the head surface are contained inside thereof is conducted, it is possible to determine one point on the brain surface in response to an arbitrary point on the head surface by the use of the minimum distance search method. All the procedures described above can be executed as a software program.

Another preferred aspect of the present invention relates to a software program based on a method wherein images of a plurality of markers set up at positions on head surface and brain surface images are simultaneously taken in order to project the positions on the head surface onto the positions on the brain surface underlying the head surface, and the positions on the brain surface underlying the positions on the head surface at which the respective markers are positioned are determined by the perpendicular projection method.

In the perpendicular projection method, a plane being in contact with an arbitrary point on the head surface in a three-dimensional head region image is drawn, and a vertical line is drawn downwards from the contact point on the plane to the brain surface, whereby an intersection point with the brain surface is determined as a projection point. Although the present method is also applicable for an unprocessed head region image and a smoothened head region image, it is more effective in case of using a head surface image fitted to a convex polyhedron/convex hull. In the case where a vertical line is drawn downwards from an arbitrary point on the head surface image fitted to the convex polyhedron/convex hull to the brain surface, when the vertical line is superposed to an original image of the brain surface to determine an intersection point with the vertical line, it is also possible to determine more accurate coordinates of the brain surface and head surface points. All the procedures described here can be executed as a software program.

A still further preferred aspect of the present invention relates to a software program based on a method wherein images of a plurality of markers set up at positions on head surface and brain surface images are simultaneously taken in order to project the positions on the head surface onto the positions on the brain surface underlying the head surface, and the positions on the brain surface underlying the positions on the head surface at which the respective markers are positioned are determined by the head surface/brain interior reference dotted line segment connecting method.

In the head surface/reference dotted line segment connecting method, a straight line is drawn from an arbitrary point on the head surface in the three-dimensional head region image to a reference point inside the brain surrounded by the head surface, and an intersection point of the straight line and the brain surface is determined as a projection point for the head surface point in question. The reference point inside the brain is an arbitrary point or a set of points. For instance, it is also effective that a weighted center point of the head surface or the brain surface is set up to the reference point. Alternatively, It is possible that the reference point is set up to a specific brain structure such as an anterior commissure. It is also possible that the reference point is set up to the weighted center point on the head surface in the vicinity centering around an arbitrary point on the head surface, and the point on the head surface in question is deviated to obtain a set of reference points. The present method is applicable to any of an unprocessed head region image, a smoothened head region image, and a head surface image fitted to a polyhedron/hull. All the procedures described here can be executed as a software program.

In the present invention, the above-described method wherein arbitrary points on a head surface in a three-dimensional head region image are projected onto a brain surface may be expanded in such that it projects not only one point, but also a certain region of the head surface as a set of points, moreover the whole surface thereof. These procedures can also be executed as a software program.

In the present invention, the above-described method wherein arbitrary points on a head surface in a three-dimensional head region image are projected onto a brain surface is also applicable in the case where arbitrary points on a brain surface are projected onto a head surface; and the procedures therefor may also be executed as a software program.

For achieving the second object, when standard points on a head surface have been previously expressed on a variety of three-dimensional brain surface coordinates by using these methods, and further probability distributions of these standard points and projected points on brain surfaces have been determined with respect to a plurality of subjects, it becomes possible to express arbitrary positions on a head surface onto arbitrary three-dimensional coordinates with probability error information without accompanying taking auxiliary brain images. As a result, all the procedures can be built in a software program.

Although international 10-20 system standard points recommended by International Federation of Societies for Electroencephalography Clinical Neurophysiology and its expanded method are preferably used as standard points on a head surface, the other relative brain surface coordinate system may also be used.

In the present invention, it is also possible that a distance distribution between a head surface and a brain surface is obtained by applying the above-described method wherein arbitrary points on the head surface in a three-dimensional head region image are projected on the brain surface.

An arbitrary point other than standard points on a head surface may be described on the basis of a relative positional relationship with respect to the standard points. Although international 10-20 system standard points recommended by International Federation of Societies for Electroencephalography and Clinical Neurophysiology and its expanded method are preferably used as the standard points, standard points in the other relative brain surface coordinate system may also be used. Furthermore, although the plurality of the markers are set up at the positions on a head surface in the above description, it may be in such that characteristic points such as ear root portion and occipital nodes are extracted from a three-dimensional head region image without setting up any marker, and then the standard points of the international 10-20 system or standard points in the other relative coordinate system are determined on the three-dimensional head region image, whereby the resulting standard points are used as virtual markers.

Projected points on the brain surface with respect to arbitrary points other than the standard points on the head surface may be described by a relative positional relationship of the standard points on the head surface with their projected points on the brain surface. It is also possible that arbitrary points other than standard points on the head surface are expressed on a head surface coordinate system, and the results are projected on the brain surface. Moreover, it is also possible that projected points on the brain surface of standard points are used to be described as positions of a coordinate system on the brain surface.

The transcranial brain function measuring apparatus for achieving the third object according to the present invention comprises a probe which have an irradiation point for irradiating radial ray or electromagnetic wave from a head surface of a subject to a interior thereof and a detection point for detecting an interaction of the irradiated radial ray or electromagnetic wave and a brain on the head surface, and a data processor for analyzing a condition of the brain based on a signal detected by the detection point of the probe. The data processor is provided with a coordinate transformation section for transforming positions on the head surface to brain surface coordinates with the use of data obtained by transforming the head surface coordinates to the brain surface coordinates in accordance with the method of the present invention, whereby a position on the head surface decided by the irradiation point and the detection point are transformed to the brain surface coordinates, and the analysis data based on the signal detected by the detection point is displayed on the transformed brain coordinates.

One example of the transcranial brain function measuring apparatus is a light measuring apparatus wherein the probe is provided with a light delivery point for emitting a light and a light reception point for receiving the light to be discharged to the outside after transmitting through and/or being reflected by the subject.

A preferred example of the light measuring apparatus is a multi-channel light measuring apparatus in which a plurality of the light delivery points and a plurality of the light reception points are disposed on the head surface, respectively.

It is preferred that the light emitted from the light delivery point to the subject is a light in a near-infared region which exhibits high permeability with respect to a living body.

In the case where an irradiation point is distant from a detection point, a position on a head surface corresponding to that on a brain surface detected by the detection point may be a central position of a straight line obtained by connecting two points of the irradiation point and the detection point.

Another preferred aspect for the transcranial brain function measuring apparatus of the present invention is the one wherein a distances between the irradiation point and the detection point is decided in such that a detection sensitivity at the detection point as a result of an interaction of the electromagnetic wave or the radial ray from the irradiation point and the brain on the surface thereof becomes the maximum on the basis of the distance distribution between the head surface and the brain surface determined by the method according to the present invention.

Advantageous Effects of the Invention

When head surface coordinates are transformed to brain surface coordinates according to the present invention, it becomes possible to project arbitrary points on the head surface onto the brain surface, so that it becomes possible that data obtained by a transcranial brain function measuring/stimulating method are projected on the brain surface with high precision in a software program. As described above, the present invention can solve the problems of distortion accompanied with a conventional sphere fitting method and the applied methods therefor.

The present invention provides extremely high scalability for processing the data obtained by the transcranial brain function measuring/stimulating method. When the data obtained by the transcranial brain function measuring/stimulating method is projected on the brain surface by using the method according to the present invention, it becomes possible that the data is transformed into a format which can be normalized and used commonly in the brain function study. Through the normalization, an integration of data among a plurality of subjects may also be simply conducted. In addition, it becomes possible to integrate the data into and compare with those obtained by the other brain function measuring methods. Thus, the present invention provides a novel technology which becomes a foundation with respect to a propagation of the transcranial brain function measuring/stimulating method such as NIRS and TMS, so that it makes a remarkable contribution to developments in brain function studies and their clinical applications.

In the present invention, when coordination of standard points on a head surface with those three-dimensional brain surface projection points is previously conducted, it becomes possible to project data obtained by the transcranial brain function measuring/stimulating method onto the brain surface without taking three-dimensional head region images. Besides, it becomes possible to clearly obtain spatial error information as to the projection.

Transformation of standard points on a head surface to a brain surface three-dimensional coordinates may be expressed as a probability distribution based on measurement data of a plurality of subjects. Furthermore, when a center of the probability distribution is used, it is also possible to determine one position of the corresponding brain surface three-dimensional coordinates with respect to one standard point on the brain surface.

With respect to arbitrary points on a head surface, when a relative positional relationship with near three points of standard points on the head surface is determined, it is possible to project the head surface onto the brain surface underlying the head surface by referring to the positions of the standard points projected on the brain surface. These procedures can also be executed on a software program.

Thus, it becomes possible to project points on the head surface onto the brain surface according to the software program based on the present invention in either a case where a three-dimensional head region image is obtained, or a case where such image is not obtained. A method by which arbitrary positions on a head surface can be projected on a brain surface without taking any three-dimensional head region image has never been known. Accordingly, the present invention is a method for providing quite novel advantages. However, a software program for expressing a two-dimensional map of data measured by means of NIRS of a brain surface has been known, the method of this software is not based on a manner for correct coordination of respective pixels in the two-dimensional map with voxels on a three-dimensional coordinate. Hence, the present invention is extremely effective for realizing a more correct brain function image analysis.

According to the transcranial brain function measuring apparatus of the present invention, it becomes possible to correctly display analytical data on a brain surface coordinate. For instance, NIRS measurement data expressed on a two-dimensional relative coordinate can be projected correctly on a brain surface in three-dimensional space, and they may be expressed as the data on three-dimensional coordinate axes in even such an actual situation that measurement data is expressed as points or a map on a two-dimensional plane in case of NIRS data. Therefore, the present invention provides an extremely effective display manner.

EXPLANATION OF SYMBOLS 4 light delivery point
6 light reception point
12 probe
18 data processor
14 light source
16 detector
20 display unit

DETAILED DESCRIPTION OF AN EXEMPLARY EMBODIMENT

Figure 1:
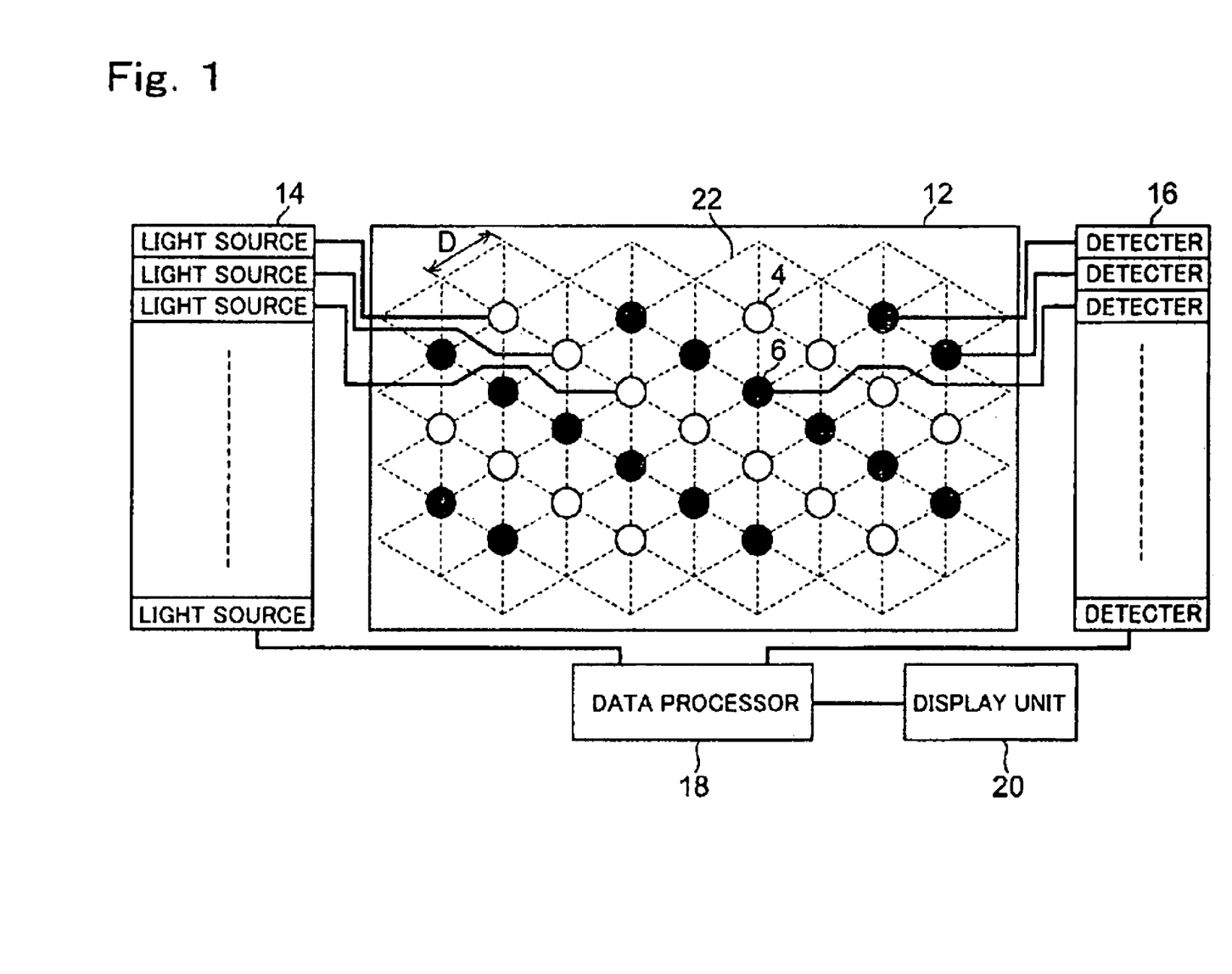
FIG. 1 is a block diagram showing schematically a multi-channel light measuring system according to one example.

FIG. 1 is a block diagram showing schematically a multi-channel light measuring system as an example of the transcranial brain function measuring apparatus. The multi-channel light measuring system is provided with a probe 12 wherein a plurality of light delivery points 4 from which the light is emitted to a subject, and a plurality of light reception points 6 by which the light after transmitting the subject and/or being reflected thereby and then being emitted to the outside is received are disposed, respectively, on a surface of disposition; and a data processor 18 for implementing an analysis based on the light received by the light reception points 6 in the probe 12.

Reference numeral 14 denotes a light source for supplying a light for measurement to the respective light delivery points. A light emitting element such as LED (light emitting diode), and LD (laser diode) may be used as the light source. A light from each of the light source 14 is guided to each of the light delivery points 4 through a light guide path such as an optical fiber wherein the light delivery point 4 is a light delivery end surface of the light guide path.

Reference numeral 16 denotes a detector for detecting the light received by each of the light reception points wherein a photo-multiplier or the like may be used as the detector as well as a light receiving element such as a photodiode or a phototransistor. A light from each of the light reception points is guided to each of the detectors 16 through a light guide path such as an optical fiber wherein the light reception point is a light input end surface of the light guide path.

Alternatively, light emitting elements may be arranged at the light delivery points 4, or light receiving elements may be arranged at the light reception points 6.

Configurations of the light delivery points 4 and the light reception points 6 in the probe 12 are not particularly limited. In an example, the light delivery points 4 and the light reception point 6 are disposed on points of grids 22 each of which divides a surface of disposition into an area composed of adjacent triangles to each other. In this case, it is arranged in such that two light delivery points 4 or two light reception points 6 are positioned on a side of each of the triangles, while one each of the light delivery point 4 and the light reception point 6 are positioned on the other two sides. In the present example, an area on the surface of disposition divided with the grids 22 is a regular triangle.

Reference numeral 18 denotes the data processor for implementing an analysis based on the light received by the light reception points 6 in the probe 12, and reference numeral 20 denotes a display unit for displaying results processed by the data processor 18.

The light delivery points 4 and the light reception points 6 are disposed on a head surface. Position coordinates of standard points on a head surface and position coordinates on a brain surface underlying the positions of the respective standard points are registered in the data processor 18 as data. Concerning a pair of the light delivery point 4 and the light reception point 6, when a light emitted from the light delivery point 4 is reflected by the brain surface and received by the light reception point 6, the reflection point on the brain surface is a point underlying a point on a line obtained by connecting the light delivery point 4 with the light reception point 6 in the pair of the points on the head surface. Coordinates of the points on the brain surface are determined by the data processor 18 based on data indicating a relationship between position coordinates of standard points on the head surface and position coordinates on the brain surface underlying the head surface.

In the multi-channel light measuring system of the present example, data collection in each set of the light delivery points 4 and the light reception points 6 can be executed without any accompanying cross talk, when operations of the light sources 14 and the detectors 16 are changed over sequentially in every set of the light delivery point 4 and the light reception point 6.

Figure 2:
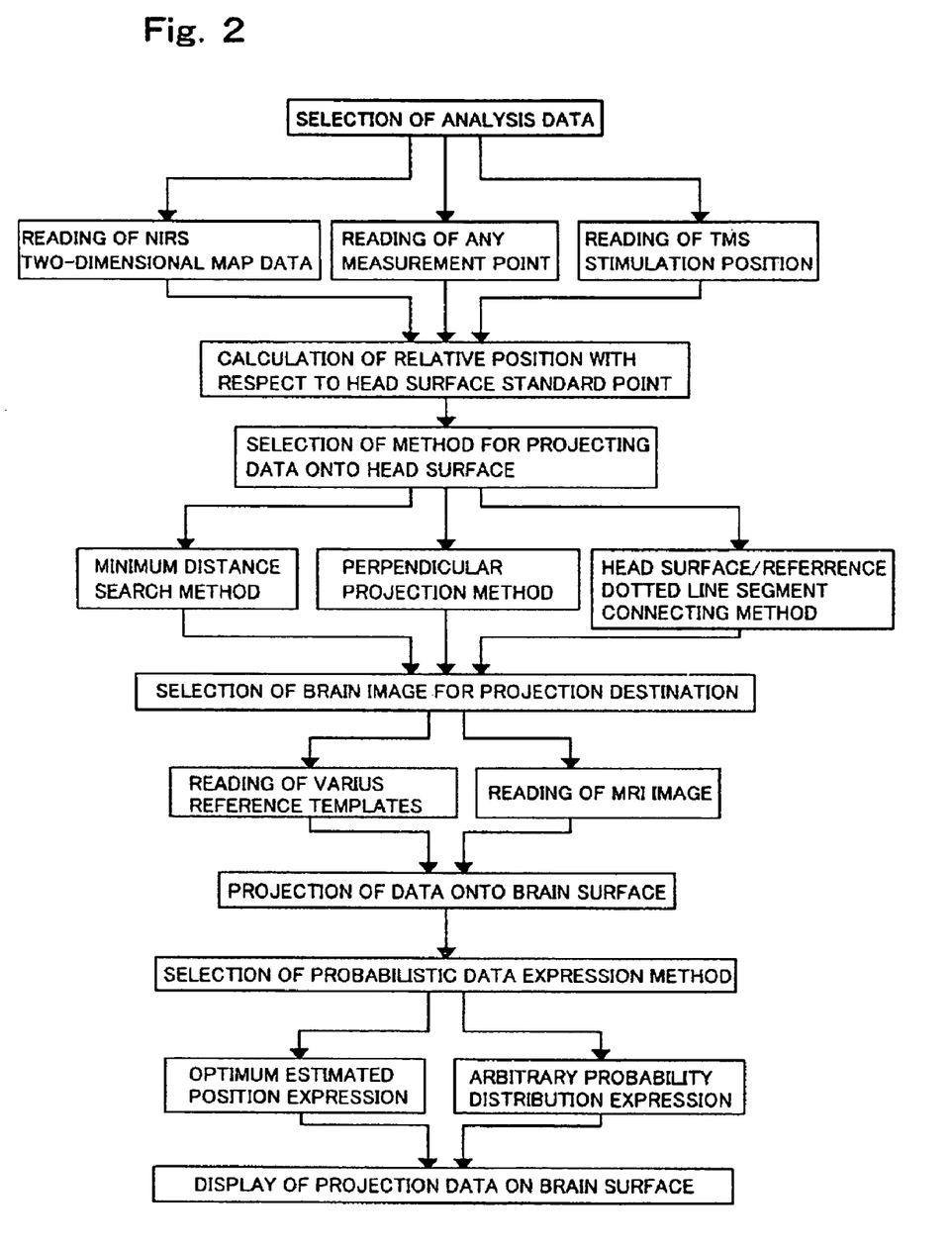
FIG. 2 is a flowchart showing schematically a software program according to one example.

FIG. 2 is a flowchart showing a flow of a software program for analyzing integrative transcranial brain function measuring/stimulating data according to the present method. The software program represented by the flowchart is a preferred example of the present invention.

Now, it is assumed that there are prepared NIRS two-dimensional map data, data at arbitrary measurement points, and stimulation position data of TMS as analyzed data. First, any of analyzed data is selected, and mutual positions between the measured points and the standard points on the head surface are calculated. Then, a method for projecting data onto the head surface is selected wherein there is prepared a minimum distance search method, a perpendicular projection method, or a head surface/brain interior reference dotted line segment connecting method as an example of the method for projecting data onto the head surface. The details of these projection methods will be mentioned later by referring to FIGS. 3 to 5. A standard template or a MRI image is selected as a brain image for a projection destination, and data is projected on the brain surface of the selected brain image in accordance with the data projection method which has been selected previously. In order to display the projected data, a probability data expression method is selected from an optimum estimated position expression method and arbitrary probability distribution expression methods, and the projected data on the brain surface is displayed in accordance with the expression method selected.

Figure 3:
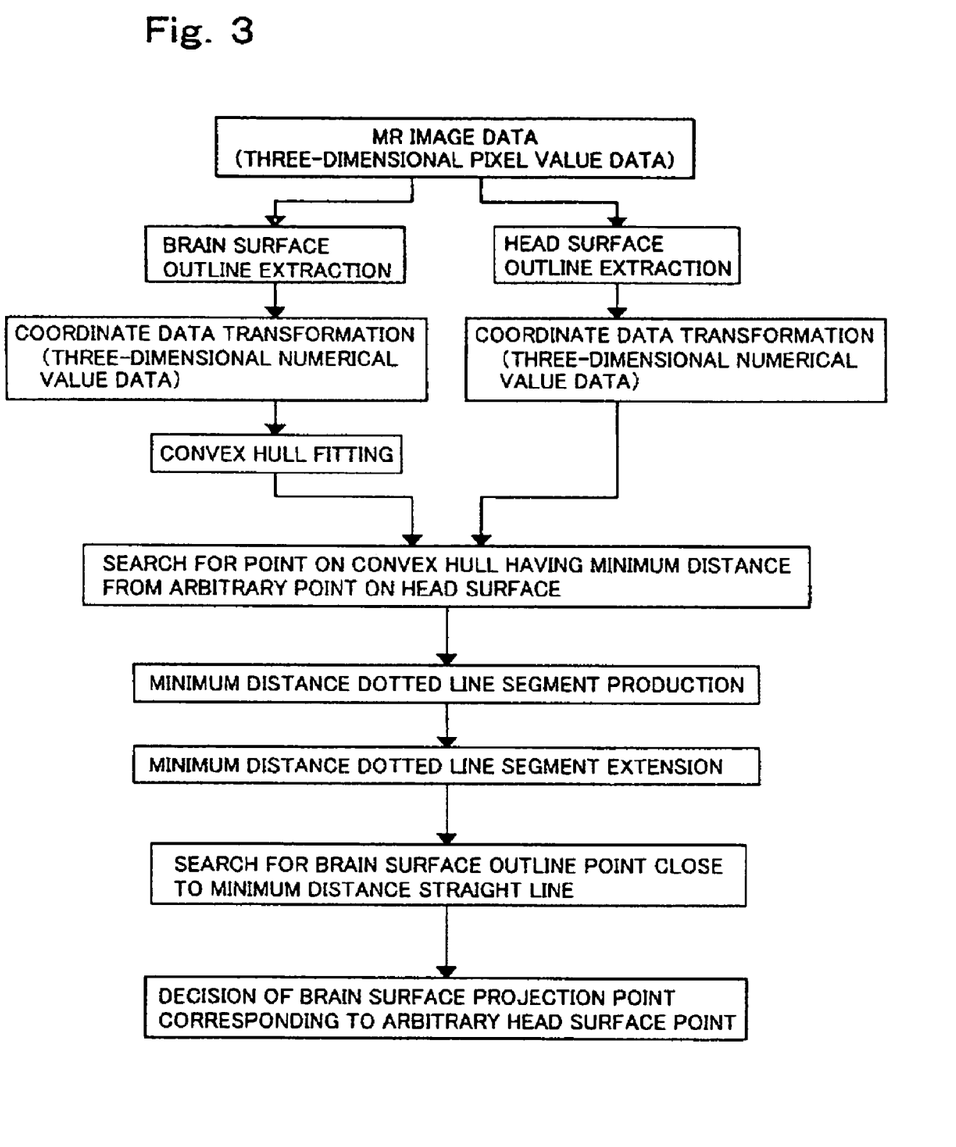
FIG. 3 is a flowchart showing schematically a minimum distance search method.

The minimum distance search method will be described in reference to FIG. 3.

It is assumed that MRI image data is prepared as three-dimensional pixel value data. First, parts which will constitute outlines of the brain surface and the head surface are extracted from MRI image data. Then, the respective pixel value data are converted to coordinate data to obtain a list of three-dimensional numerical value data. Furthermore, convex hull fitting for wrapping around the brain surface outline is made on the coordinate data of the brain surface outline. Such a point on the convex hull having the minimum distance from an arbitrary point on the head surface is searched, and the point is connected with a line segment. The resulting line segment having the minimum distance is extended in the direction of the brain surface to obtain a straight line. Moreover, the coordinate data of the brain surface outline obtained as described above is referred to thereby searching a point of the brain surface outline being closest to the straight line. The point of the brain surface outline obtained as a result of the search is decided as a projection point on the brain surface corresponding to an arbitrary head surface point.

Figure 4:
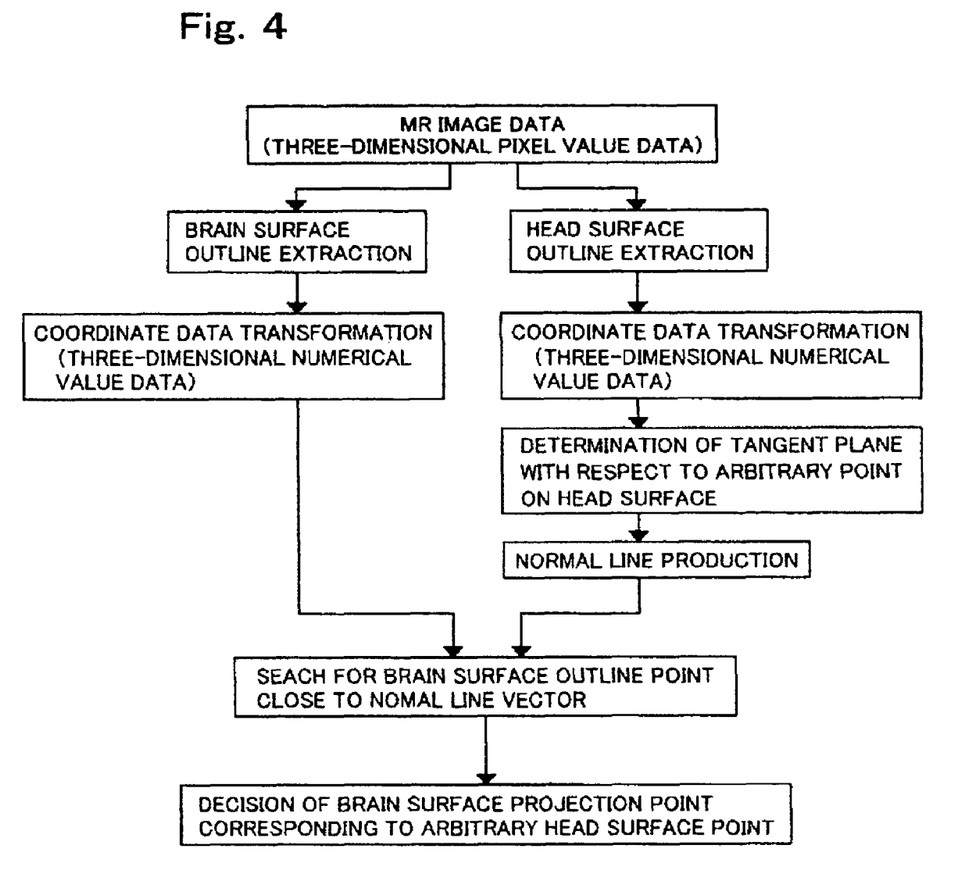
FIG. 4 is a flowchart showing schematically a perpendicular projection method.

The vertical projection method will be described by referring to FIG. 4.

It is assumed that there is prepared MRI image data as three-dimensional pixel value data. First, parts which will constitute outlines of the brain surface and the head surface are extracted from MRI image data. Then, the respective pixel value data are converted to coordinate data to obtain three-dimensional numerical value data. Furthermore, a tangent plane is determined with respect to an arbitrary point on the head surface from the coordinate data of the head surface outline, and the normal line to the tangent plane is produced. Furthermore, the coordinate data of the brain surface outline obtained as described above is referred to thereby to search a point of the brain surface outline being closest to the normal line. The point of the brain surface outline obtained as a result of the search is decided as a projection point on the brain surface corresponding to an arbitrary head surface point.

Figure 5:
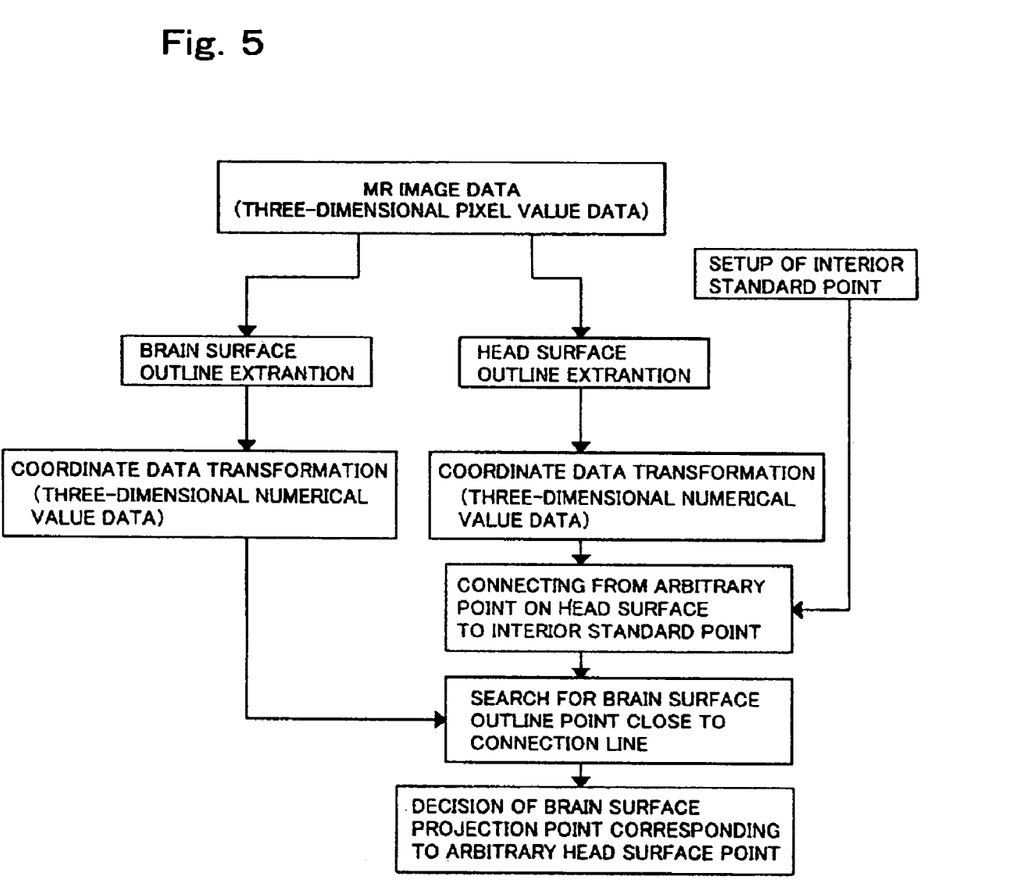
FIG. 5 is a flowchart showing schematically a head surface/reference dotted line segment connecting method.

The head surface/reference dotted line segment connecting method will be described by referring to FIG. 5.

It is assumed that there is prepared MRI image data as three-dimensional pixel value data. In addition, it is assumed that positions of inside standard points in a brain are prepared as coordinate data First, parts which will constitute outlines of the brain surface and the head surface are extracted from MRI image data. Then, the respective pixel value data are converted to coordinate data to obtain three-dimensional numerical value data. Furthermore, a line segment connecting an arbitrary point on the head surface and the inside standard point in the brain is determined with respect to coordinate data on the head surface outline. Besides, the coordinate data of the brain surface outline obtained as described above is referred to thereby to search a point of the brain surface outline being closest to the line segment. The point of the brain surface outline obtained as a result of the search is decided as a projection point on the brain surface corresponding to an arbitrary head surface point.

Although the software program may be used alone, it is either possible to incorporate a part of the software as a module into another software program, or to incorporate the whole program into still another program to build a more comprehensive software program.

EXAMPLE 1

Projection points on a brain surface are determined with respect to nineteen standard points of the international 10-20 system on a head surface. More specifically, markers are disposed on the 10-20 system standard points on a head surface of a subject, and a MRI image is taken to obtain a three-dimensional image of the head. Each of projection points on the brain surface corresponding to each of the standard points on the head surface is determined with respect to the three-dimensional image of the head in accordance with the minimum distance search method.

Furthermore, the measurement as mentioned above is conducted with respect to seventeen subjects, and the data extending over all the subjects puts together to express a probability distribution by means of MINI standard brain coordinates. Namely, head images of the respective subjects are normalized into a MINI standard brain; and a probability distribution of positions in the 10-20 system standard points of brain surface projection points after conversion by means of the normalization is expressed as a standard deviation. The results thereof are shown in Table 1.

TABLE 1

MNI brain coordinate positions of brain surface projection points in international 10-20 standard points

| | MINI Coordinates (mm) | | | Standard |
|---|---|---|---|---|
| | X | Y | Z | Deviation (mm) |
| Fp1 | −21.5 | 70.2 | −0.1 | 5.0 |
| Fp2 | 28.4 | 69.1 | −0.4 | 5.1 |
| Fz | 0.6 | 40.9 | 53.9 | 9.8 |
| F3 | −35.5 | 49.4 | 32.4 | 9.2 |
| F4 | 40.2 | 47.6 | 32.1 | 8.6 |
| F7 | −54.8 | 33.9 | −3.5 | 6.5 |
| F8 | 56.6 | 30.8 | −4.1 | 6.2 |
| Cz | 0.8 | −14.7 | 73.9 | 8.3 |
| C3 | −52.2 | −16.4 | 57.8 | 8.0 |
| C4 | 54.1 | −18.0 | 57.5 | 7.1 |
| T3 | −70.2 | −21.3 | −10.7 | 6.5 |
| T4 | 71.9 | −25..2 | −8.2 | 6.2 |
| Pz | 0.2 | −62.1 | 64.5 | 9.2 |
| P3 | −39.5 | −76.3 | 47.4 | 7.4 |
| P4 | 36.8 | −74.9 | 49.2 | 7.6 |
| T5 | −61.5 | −65.3 | 1.1 | 7.8 |
| T6 | 59.3 | −67.6 | 3.8 | 7.3 |
| 01 | −26.8 | −100.2 | 12.8 | 10.1 |
| 02 | 24.1 | −100.5 | 14.1 | 11.1 |

As described above, according to the present invention, it could have been realized that arbitrary positions on head surface were projected on the brain surface with high precision in each of the subjects. In addition, data integration among plural subjects could have been also realized. The resulting data provides such a probabilistic conclusion that 61% of each of the projected standard points on the brain surface distributes in a respective sphere with a center of the respective coordinate and a radius of its standard deviation indicated in the table in an ideal brain developed on the MNI standard brain coordinates.

Such error information is extremely useful information in study and clinical applications. More specifically, it is important to indicate an effective range in an estimation method, but not presenting uselessly the optimum value. The error information in case of projecting points on a head surface onto a brain surface is obtained without taking any MRI image in accordance with the present invention for the first time.

EXAMPLE 2

In accordance with the method of the present invention, brain activity data obtained by an actual NIRS measurement is projected on a brain surface by the use of the measuring system of FIG. 1 with taking no MRI image.

As the brain activity data, changes of an oxygenated hemoglobin concentration in a prefrontal cortex as to a case where each of ten subjects pares an apple are applied. Mutual positions of fixing points of measurement probes of the NIRS with respect to nineteen standard points of international 10-20 system have been previously measured; and then, positions of the NIRS measurement probes are obtained on the head surfaces.

Figure 6:
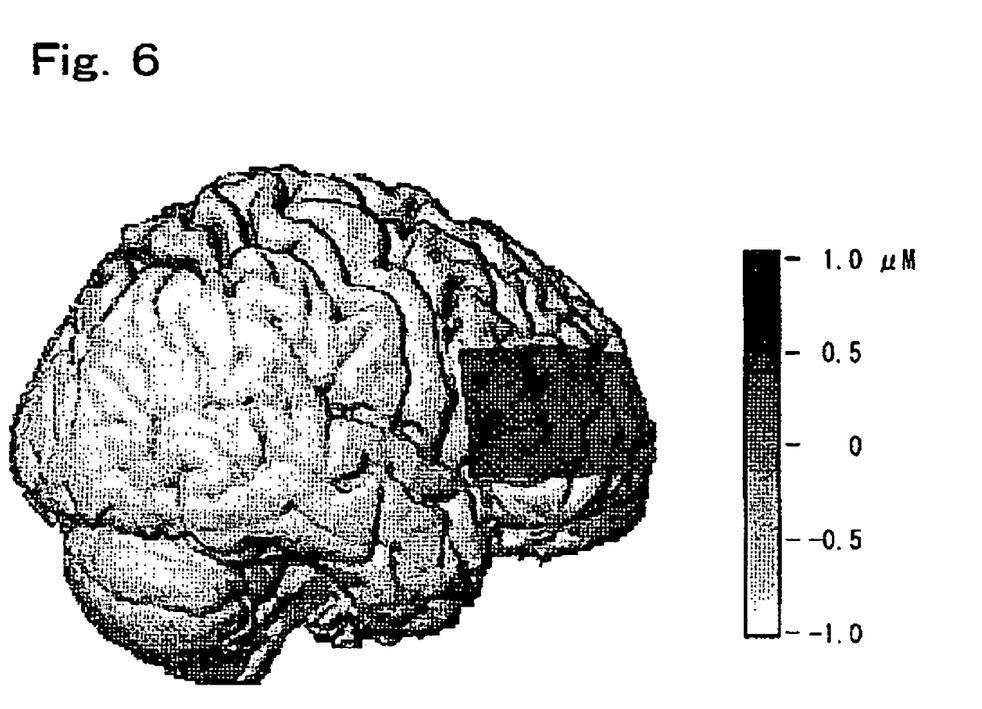
FIG. 6 is an illustration showing NIRS brain active data projected on a brain surface by referring to mutual positions with respect to standard points on a head surface without taking any MRI image.

Thereafter, coordinate information is integrated as to the ten subjects, whereby average position coordinates of the NIRS measurement probes are obtained on the head surface. These average positions are projected on a brain surface image of a typical subject by referring to the mutual position information with respect to the nineteen standard points of the international 10-20 system wherein the projection positions on the brain surface has been already definitely decided. The results thereof are shown in FIG. 6 wherein a degree of brain activity is shown with an increase in an oxygenated hemoglobin concentration indicated by an activity bar on the right side.

Although software wherein NIRS measurement data are superposed on a brain surface in accordance with a manner other than that of the present invention is commercially available, setup of a projection method is indefinite; and functions thereof cannot surpass the ones which can only superpose decoratively such measurement data onto a brain surface. On the other hand, a strict projection method can be realized based on the actual measurement values according to the method of the present invention, so that a quality being sufficient for applying the method to study and clinical purposes has been attained.

When referred to the data shown in table 1, such information that the projection method is effective with a spatial degree of accuracy from 5 mm to 10 mm in a region in question is obtained, so that a spatial error can be studied as to the results obtained.

EXAMPLE 3

Figure 7:
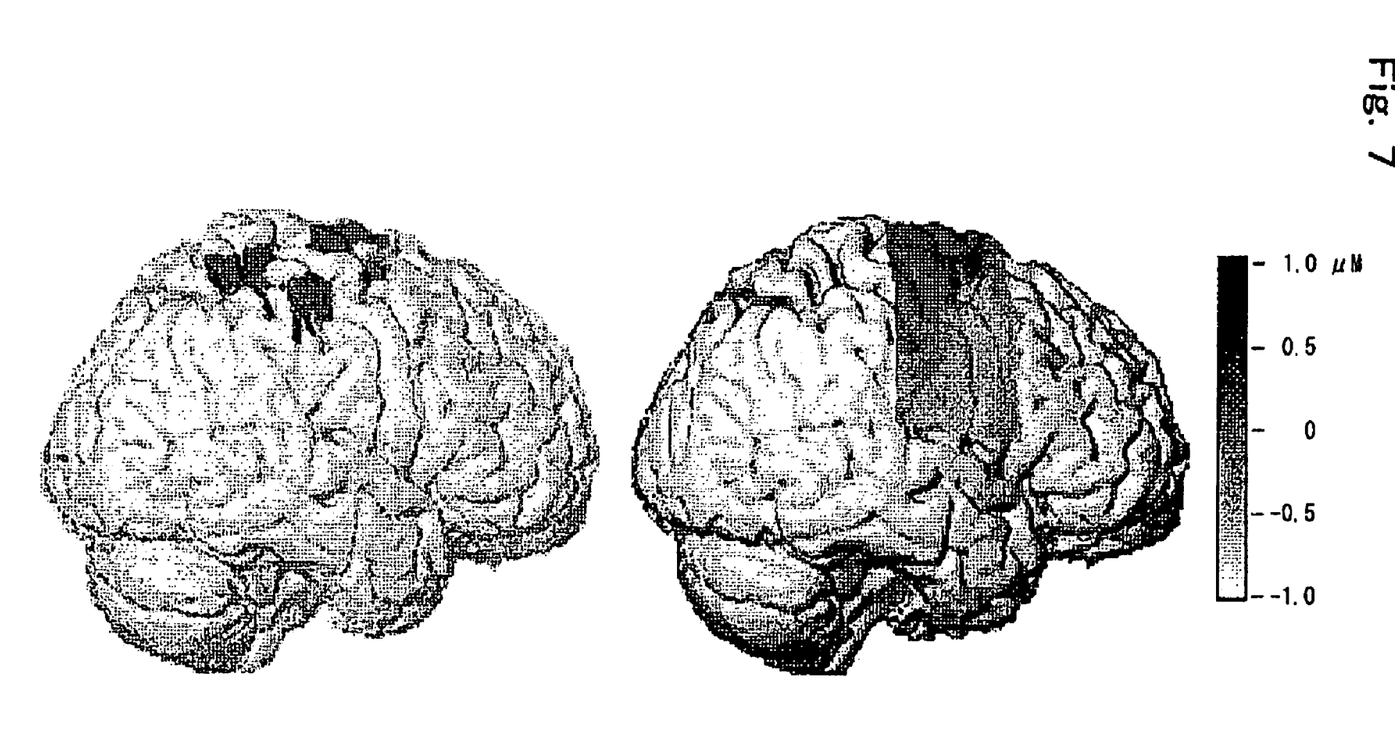
FIG. 7 is an illustration showing brain active data in case of measuring NIRS and fMRI at the same time wherein the fMRI data is shown on the left side, while the NRIS active data is shown in the right side.

In accordance with the method of the present invention, a comparison of simultaneous measurement data of a NIRS and a functional nuclear magnetic resonance apparatus (fMRI) is implemented. Activities in a motor area are measured simultaneously by means of the NIRS and the fMRI in the case where a subject pares imitatively an apple wherein measurement probes of the NIRS and position markers for indicating fixed positions of the probes have been fixed to the subject. A NIRS measurement region is projected on a brain surface image of a subject by applying the minimum distance search method according to the present invention. In the measurement by means of the fMRI, a region wherein significant decrease is observed in a reduced hemoglobin concentration is checked. In the NIRS measurement, changes in the oxygenated hemoglobin concentration are measured. Brain activity is measured based on a decrease in the reduced hemoglobin concentration in the fMRI measurement, while based on an increase in the oxygenated hemoglobin concentration in the NIRS measurement. It is known that there is a qualitative correlation between both the measurements. The results thereof are shown in FIG. 7 wherein the one shown on the left side corresponds to the fMRI data in which significant activity is observed in a region shown with charcoal. The one shown on the right side corresponds to activity data of the NRIS; and a degree of brain activity is shown by an increase in an oxygenated hemoglobin concentration indicated by the activity bar on the right side.

It has been succeeded that NIRS measurement data and fMRI measurement data are superposed on an identical brain structure image one another at a high precision in accordance with a method other than that of the present invention. In this respect, although brain function measurement using a plurality of measurement methods is going to become active in recent years, a standard method for comparing such NIRS data with that of the other brain function measuring methods has not yet been established. In this connection, it is demonstrated that an essential technology for realizing the establishment can be provided by the present invention.

EXAMPLE 4

Figure 8:
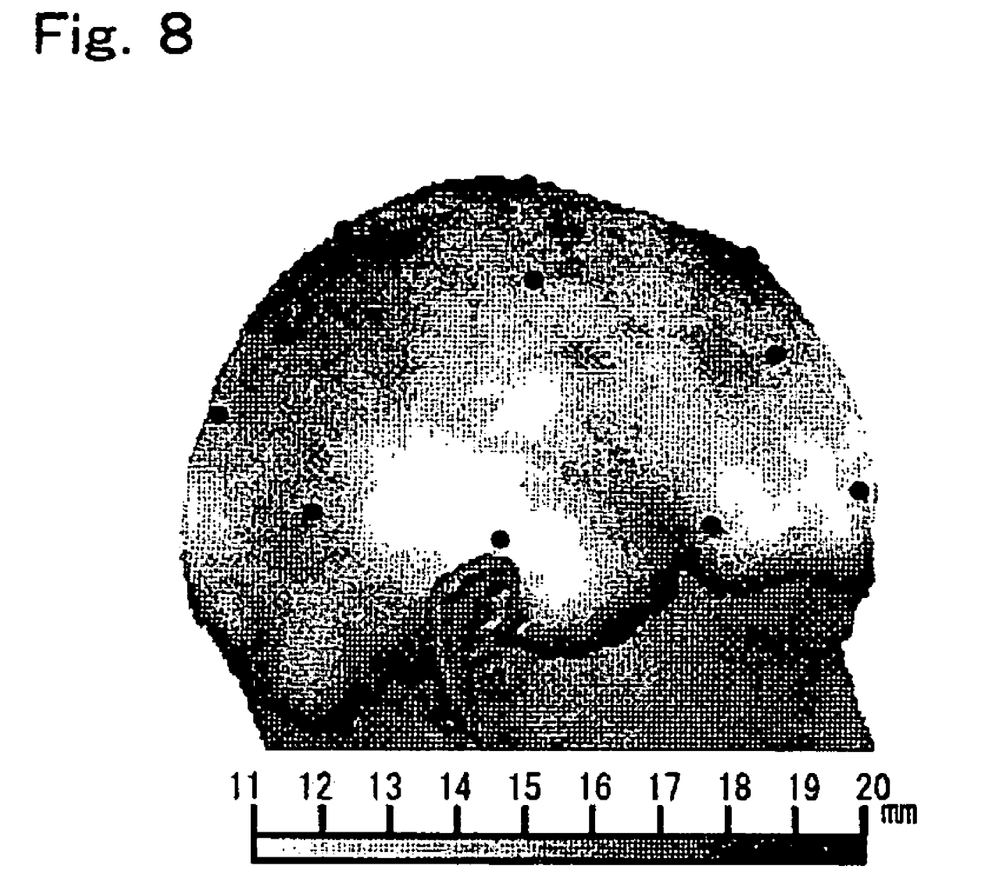
FIG. 8 is an illustration showing a distance distribution of a head surface and a brain surface wherein black dots indicate international 10-20 standard points.

A distance distribution between a head surface and a brain surface is obtained by the method according to the present invention. First, a three-dimensional image of a subject's head region is obtained by means of MRI imaging. Then, distances between the head surface and the brain surface at all points on the head surface are measured by applying the minimum distance search method, and the distance information is plotted on the brain surface. The results thereof are shown in FIG. 8.

The distance information between the head surface and the brain surface is useful for NIRS measurement Generally, in the NIRS measurement, a setup of the wider probe distance (a distance between a light delivery point and a light reception point) makes possible to measure activity in the deeper part of a brain. Since distances between the head surface and the brain surface are obtained by the present invention, useful information for setting up the NIRS probe distances is obtained. Besides, it is known that 30% of magnetic stimulation intensity of TMS is attenuated in every 1 cm increase of a distance between the head surface and the brain surface. In optimization of the TMS magnetic stimulation intensity, it is extremely useful to obtain distance information between the head surface and the brain surface; and in this respect it is demonstrated that information useful for the optimization is provided by the present invention.

INDUSTRIAL APPLICABILITY

The present invention is applicable for a method and an apparatus wherein such results measured by near-infrared spectroscopy (NIRS), a transcranial magnetic stimulation system (TMS), and other transcranial brain function measuring/stimulating methods are expressed by applying brain surface coordinates.

What is claimed is:
1. A method for transcranial measurement of brain function, comprising the steps of:
preparing image data including images of a plurality of markers at positions on a head surface and a brain surface image; and
projecting the positions at the markers on the head surface which are positioned on a three-dimensional head image in the data onto positions on the brain surface, which are positions underlying the positions on the head surface, for determining three-dimensional coordinate positions of the projected points, thereby transforming head surface coordinates to brain surface coordinates,
wherein the step for projecting the positions on the head surface onto the positions on the brain surface is carried out by a minimum distance search method or a head surface/brain interior reference dotted line segment connecting method,
the minimum distance search method being a method which comprises the steps of:
(a) providing MRI image data including three-dimensional pixel value data of the brain surface and the head surface,
(b) extracting outlines of the brain surface and the head surface from the MRI image data,
(c) smoothing the extracted brain surface outline,
(d) searching a point on the smoothing processed brain surface outline having the minimum distance from an arbitrary point on the head surface outline,
(e) connecting the searched point on the smoothing processed brain surface outline to the arbitrary point with a line segment,
(f) searching a point of the extracted brain surface outline being closest to a straight line extending from the line segment in the direction of the brain surface, the extracted brain surface outline being not subjected to the smoothing step (c), and
(g) deciding the point obtained by searching step (f) as a projection point on the brain surface corresponding to the arbitrary point on the head surface, and
the head surface/brain interior reference dotted line segment connecting method being a method in which a straight line is drawn from an arbitrary point on the head surface in the three-dimensional head image to a reference point inside the brain surrounded by the head surface, and an intersection point of the straight line and the brain surface is determined as a projection point for the head surface point in question.
2. The method according to claim 1, further comprising a step for normalizing the brain surface coordinates obtained from a plurality for subjects onto a standard brain.
3. The method according to claim 1, wherein the respective markers are not actually set up at the head surface, but they are calculated from head figure information to be virtually set up.
4. The method according to claim 1,
previously determining projected positions on the brain surface underlying positions to be standard points as the markers on the head surface by the step for projecting the positions on the head surface onto the positions on the brain surface; and
further comprising a step of calculating coordinates of arbitrary points or a set of the points on the head surface from relative positions with respect to the standard points on the head surface for determining their projected points or a set of the points on the brain surface.
5. The method according to claim 1,
previously determining projected positions on the brain surface underlying positions to be standard points as the markers on the head surface by the step for projecting the positions on the head surface onto the positions on the brain surface;

further comprising steps of previously determining a probability distribution of the projected positions on the brain surface of the standard points from data of a plurality of subjects, and determining brain surface coordinates obtained by projecting arbitrary points on the head surface onto the brain surface based on the standard points and their probability error information.

6. The method according to claim 1, further comprising a step of determining a distance distribution between the head surface and the brain surface from head surface coordinates and the brain surface coordinates determined by the step for projecting the positions on the head surface onto the positions on the brain surface.

7. A software program implemented on a computer for realizing the method according to claim 1.

8. The method according to claim 1,
wherein the image data is that obtained by simultaneously taking images of a plurality of markers set up at positions on the head surface and the brain surface image.

9. A transcranial brain function measuring apparatus comprising:
a probe having an irradiation point for irradiating a radial ray or an electromagnetic wave from a head surface of a subject to a interior thereof and a detection point for detecting an interaction of the irradiated radial ray or electromagnetic wave and a brain on the head surface; and a data processor for analyzing a condition of the brain based on a signal detected by the detection point of the probe, wherein the data processor is provided with a coordinate transformation section for transforming head surface coordinates to brain surface coordinates with data obtained by projecting positions on the head surface onto respective positions on the brain surface, whereby a position on the head surface decided by the irradiation point and the detection point are transformed to the brain surface coordinates, and the analysis data based on the signal detected by the detection point is displayed on the transformed brain surface coordinates, and wherein the data obtained by projecting positions on the head surface onto respective positions on the brain surface is obtained by a minimum distance search method or a head surface/brain interior reference dotted line segment connecting method, the minimum distance search method being a method which comprises the steps of:
(a) providing MRI image data including three-dimensional pixel value data of the brain surface and the head surface,
(b) extracting outlines of the brain surface and the head surface from the MRI image data,
(c) smoothing the extracted brain surface outline,
(d) searching a point on the smoothing processed brain surface outline having the minimum distance from an arbitrary point on the head surface outline,
(e) connecting the searched point on the smoothing processed brain surface outline to the arbitrary point with a line segment,
(f) searching a point of the extracted brain surface outline being closest to a straight line extending from the line segment in the direction of the brain surface, the extracted brain surface outline being not subjected to the smoothing step (c), and
(g) deciding the point obtained by searching step (f) as a projection point on the brain surface corresponding to the arbitrary point on the head surface, and
the head surface/brain interior reference dotted line segment connecting method being a method in which a straight line is drawn from an arbitrary point on the head surface in the three-dimensional head image to a reference point inside the brain surrounded by the head surface, and an intersection point of the straight line and the brain surface is determined as a projection point for the head surface point in question.

10. The transcranial brain function measuring apparatus according to claim 9, wherein the transcranial brain function measuring apparatus is a light measuring apparatus; and the probe is provided with light delivery point(s) as the irradiation points for emitting light and light reception point(s) as the detection points for receiving the light to be discharged to the outside after transmitting through and/or being reflected by the subject.

11. The transcranial brain function measuring apparatus according to claim 10, wherein the light measuring apparatus is a multi-channel light measuring apparatus in which a plurality of the light delivery points and a plurality of the light reception points are disposed on the head surface, respectively.

12. The transcranial brain function measuring apparatus according to claim 11, wherein the light emitted from the light delivery points to the subject is a light in a near-infrared region.

13. The transcranial brain function measuring apparatus according to claim 11, wherein the position on the head surface determined by the irradiation point and the detection point corresponds to the central position along a straight line connecting these two points to each other.

14. The transcranial brain function measuring apparatus according to claim 9,
wherein a distance between the irradiation point and the detection point is decided in such that a detection sensitivity at the detection point as a result of an interaction of the electromagnetic wave or the radial ray from the irradiation point and the brain on the surface thereof becomes the maximum on the basis of the distance distribution between the head surface and the brain surface determined in claim 6.

* * * * *